(12) United States Patent
Moulton et al.

(10) Patent No.: US 9,056,182 B2
(45) Date of Patent: Jun. 16, 2015

(54) CATHETER HAVING A PRESSURE ACTIVATED SPLITTABLE FEATURE

(75) Inventors: William G. Moulton, West Jordan, UT (US); Justin G. Hortin, Farmington, UT (US); Jeffrey R. McMurray, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 458 days.

(21) Appl. No.: 13/216,029

(22) Filed: Aug. 23, 2011

(65) Prior Publication Data

US 2013/0053825 A1  Feb. 28, 2013

(51) Int. Cl.
*A61M 25/00* (2006.01)
*A61M 25/06* (2006.01)
*A61M 25/01* (2006.01)

(52) U.S. Cl.
CPC ....... *A61M 25/0074* (2013.01); *Y10T 29/49826* (2015.01); *A61M 25/0668* (2013.01); *A61M 2025/0188* (2013.01)

(58) Field of Classification Search
CPC .......... A61B 17/3417; A61M 25/0668; A61M 25/0074; A61M 2025/0188
USPC .................. 604/160, 164.05, 164.1, 264, 523
See application file for complete search history.

(56) References Cited

U.S. PATENT DOCUMENTS

| | | |
|---|---|---|
| 3,713,442 A | 1/1973 | Walter |
| 4,563,180 A | 1/1986 | Jervis et al. |
| 4,661,094 A | 4/1987 | Simpson |
| 4,717,381 A | 1/1988 | Papantonakos |
| 4,784,638 A | 11/1988 | Ghajar et al. |
| 4,961,731 A | 10/1990 | Bodicky et al. |
| 4,968,307 A | 11/1990 | Dake et al. |
| 5,037,403 A | 8/1991 | Garcia |
| 5,085,635 A | 2/1992 | Cragg |
| 5,088,991 A | 2/1992 | Weldon |
| 5,201,723 A | 4/1993 | Quinn |
| 5,234,406 A | 8/1993 | Drasner et al. |
| 5,250,034 A | 10/1993 | Appling et al. |
| 5,267,979 A | 12/1993 | Appling et al. |
| 5,334,154 A | 8/1994 | Samson et al. |
| 5,380,307 A | 1/1995 | Chee et al. |
| 5,536,261 A | 7/1996 | Stevens |
| 5,542,925 A | 8/1996 | Orth |
| 5,578,006 A | 11/1996 | Schön |
| 5,616,137 A | 4/1997 | Lindsay |

(Continued)

FOREIGN PATENT DOCUMENTS

| | | |
|---|---|---|
| EP | 0 299 622 A2 | 6/1988 |
| EP | 0 947 211 A2 | 10/1999 |
| WO | WO 01/91830 A1 | 12/2001 |

OTHER PUBLICATIONS

Weber, Paul W. et al., "AJR: Modified Catheter Can Reduce Contrast Material Injuries," Health Imaging.com, Clinical Studies, http://www.healthimaging.com/index.php?view=article&id=18807%3Aajr-modified-cath . . . , 1 page, Oct. 21, 2009.

*Primary Examiner* — Kami A Bosworth
(74) *Attorney, Agent, or Firm* — Jeanne Lukasavage; Craig Metcalf; Kirton McConkie

(57) ABSTRACT

A catheter having a catheter body with a lumen and a distal lumen opening. The catheter's lumen extends through the catheter body along a longitudinal axis of the catheter body. A splittable feature is formed within a wall of the catheter body.

14 Claims, 9 Drawing Sheets

(56) References Cited

U.S. PATENT DOCUMENTS

| | | |
|---|---|---|
| 5,647,846 A | 7/1997 | Berg et al. |
| 5,830,181 A | 11/1998 | Thornton |
| 5,843,017 A | 12/1998 | Yoon |
| 5,857,464 A | 1/1999 | Desai |
| 6,052,612 A | 4/2000 | Desai |
| 6,129,700 A | 10/2000 | Fitz |
| 6,132,405 A | 10/2000 | Nilsson et al. |
| 6,293,958 B1 | 9/2001 | Berry et al. |
| 6,508,966 B1 * | 1/2003 | Castro et al. ............ 264/138 |
| 6,514,236 B1 | 2/2003 | Stratienko |
| 6,547,769 B2 | 4/2003 | VanTassel et al. |
| 6,641,564 B1 | 11/2003 | Kraus |
| 6,669,679 B1 | 12/2003 | Savage et al. |
| 6,866,655 B2 | 3/2005 | Hackett |
| 7,108,674 B2 | 9/2006 | Quinn |
| 7,144,386 B2 * | 12/2006 | Korkor et al. ............ 604/164.03 |
| 8,262,619 B2 * | 9/2012 | Chebator et al. ......... 604/164.05 |
| 2002/0072712 A1 | 6/2002 | Nool et al. |
| 2003/0023200 A1 | 1/2003 | Barbut et al. |
| 2005/0124969 A1 | 6/2005 | Fitzgerald et al. |
| 2005/0197633 A1 | 9/2005 | Schwartz et al. |
| 2006/0184048 A1 | 8/2006 | Saadat |
| 2007/0073271 A1 | 3/2007 | Brucker et al. |
| 2007/0225659 A1 * | 9/2007 | Melsheimer ................ 604/264 |
| 2009/0030374 A1 * | 1/2009 | Osypka .................... 604/164.05 |
| 2010/0286657 A1 | 11/2010 | Heck |
| 2012/0022502 A1 | 1/2012 | Adams et al. |

* cited by examiner

CATHETER HAVING A PRESSURE ACTIVATED SPLITTABLE FEATURE

BACKGROUND

Vascular access devices are used for communicating fluid with the anatomy of a patient. For example, vascular access devices, such as catheters, are commonly used for infusing fluid, such as saline solution, various medicaments, and/or total parenteral nutrition, into a patient, withdrawing blood from a patient, and/or monitoring various parameters of the patient's vascular system.

A variety of clinical circumstances, including massive trauma, major surgical procedures, massive burns, and certain disease states, such as pancreatitis and diabetic ketoacidosis, can produce profound circulatory volume depletion. This depletion can be caused from actual blood loss or from internal fluid imbalance. In these clinical settings, it may be necessary to infuse blood and/or other fluid rapidly into a patient to avert serious consequences.

Additionally, the ability to inject large quantities of fluid in a rapid manner may be desirable for certain other medical and diagnostic procedures. For example, some diagnostic imaging procedures utilize contrast media enhancement to improve lesion conspicuity in an effort to increase early diagnostic yield. These procedures necessitate that viscous contrast media be injected by a specialized "power injector" pump intravenously at very high flow rates, which establishes a contrast bolus or small plug of contrast media in the bloodstream of the patient which results in enhanced image quality.

Power injection procedures generate high pressures within the infusion system, thereby requiring some specialized vascular access devices, extension sets, media transfer sets, pump syringes, and bulk or pre-filled contrast media syringes. As the concentration (and thereby viscosity) and infusion rate of the contrast media are increased, bolus density also increases resulting in better image quality via computed tomography (CT) attenuation. Therefore, a current trend in healthcare is to increase the bolus density of the contrast media by increasing both the concentration of the contrast media and the rate at which the media is infused into the patient, all of which ultimately drives system pressure requirements higher.

Intravenous infusion rates may be defined as either routine, generally up to 999 cubic centimeters per hour (cc/hr), or rapid, generally between about 999 cc/hr and 90,000 cc/hr (1.5 liters per minute) or higher. For some diagnostic procedures utilizing viscous contrast media, an injection rate of about 1 to 10 ml/second is needed to ensure sufficient bolus concentration. Power injections of viscous media at this injection rate produce significant back pressure within the infusion system that commonly results in a failure of the infusion system components.

Traditionally, rapid infusion therapy entails the use of an intravenous catheter attached to a pump, such as a peristaltic pump, and a fluid source. A patient is infused as a tip portion of the catheter is inserted into the vasculature of a patient and the pump forces a fluid through the catheter and into the patient's vein. Current rapid infusion therapies utilize a catheter and catheter tip with geometries identical to those used with traditional, routine infusion rates. These geometries may include a tapering catheter tip such that the fluid is accelerated as the fluid moves through the catheter tip and exits into a patient's vasculature. This acceleration of the infused fluid is undesirable for several reasons.

For example, the tapered catheter results in a greater backpressure for the remainder of the catheter assembly. This effect is undesirable due to the limitations of the pumping capacity of the infusion pump as well as the limited structural integrity of the components and subcomponents of the infusion system. For example, if the backpressure becomes too great, the pump's efficiency may decrease and certain seals or connections within the infusion system may fail. Additionally, the fluid acceleration in the catheter tip results in a recoil force that may cause the catheter tip to shift within the patient's vein thereby displacing the catheter and/or damaging the patient's vein and/or injection site. Fluid acceleration also increases the jet velocity of the infusate at the tip of the catheter. In some procedures, the fluid jet may pierce the patient's vein wall thereby leading to extravasation or infiltration. Not only is this uncomfortable and painful to the patient, but infiltration may also prevent the patient from receiving the needed therapy.

To overcome undesirable backpressures and increased acceleration of infused fluids, some intravascular systems include arrays of diffusion holes provided in and around the tip portion of the intravenous catheter. In general, diffusion holes increase the surface area of the catheter tip opening thereby decreasing fluid pressure at the catheter tip opening. However, addition of diffusion holes at or near the tip of a catheter also reduces buckling resistance of the catheter thereby making the catheter tip more susceptible to crushing during insertion. As a result, the addition of diffuser holes may result in failed catheterization and physical pain to the patient. Further, addition of diffuser holes provides the catheter with a non-continuous outer surface that may snag or catch on the opening of the patient's skin and/or vein through which the catheter is inserted. This too may result in failed catheterization, physical pain and/or physical damage to the patient.

Thus, while methods and systems currently exist to reduce exit velocity of an infusate during rapid infusion procedures, challenges still exist. Accordingly, it would be an improvement in the art to augment or even replace current techniques with other techniques.

BRIEF SUMMARY OF THE INVENTION

The systems and methods of the present disclosure have been developed in response to problems and needs in the art that have not yet been fully resolved by currently available infusion systems and methods. Thus, these systems, components, and methods are developed to provide for safer and more efficient rapid infusion procedures.

One aspect of the invention provides an improved vascular access device for use in combination with a vascular infusion system capable of rapidly delivering an infusate to the vascular system of a patient. Some embodiments of the invention can be configured as follows. The vascular access device can include an intravenous catheter configured to access the vascular system of a patient. The intravenous catheter can have a lumen extending therethrough along a longitudinal axis to a distal lumen opening. The tip portion can comprise a tapered portion, wherein the outer and inner surface of the tip taper towards the distal end of the catheter. The tapered portion of the intravenous catheter can be modified to include a splittable feature formed though a wall of the catheter body, wherein upon the lumen of the catheter being subjected to increased fluid pressure, the splittable feature is enabled thereby increasing the effective area of the catheter's distal opening.

In another aspect of the invention, a catheter has a catheter body, which has a lumen and a distal lumen opening. The lumen can extend through the catheter body along a longitudinal axis of the catheter body to the distal lumen opening. The catheter can also have a splittable feature formed through a distal tapered portion of the catheter body. In some implementations, the splittable feature is a line of perforation holes. In other implementations, the splittable feature is a skive line.

In yet another aspect of the invention, a peripheral catheter includes a catheter body that has a lumen and a distal lumen opening. The lumen extends through the catheter body along a longitudinal axis of the catheter body. In some implementations of the present invention, the catheter body has a truncated length sufficient to access a peripheral vein of a patient, and the catheter body is sized smaller than or equal to a fourteen gauge catheter. A splittable feature is formed through a distal, tapered portion of the catheter body.

Further, in some implementations of the present invention a method for manufacturing a catheter having a splittable feature is provided. The steps of the method include providing a catheter body having an outer surface, an inner surface, a proximal end, a distal end, a lumen extending between the proximal and distal ends along a longitudinal axis of the catheter body, and a distal lumen opening; providing a catheter tip forming a portion of the distal end, the catheter tip including the distal lumen opening; and providing a splittable feature formed within a wall of the catheter tip.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

Embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
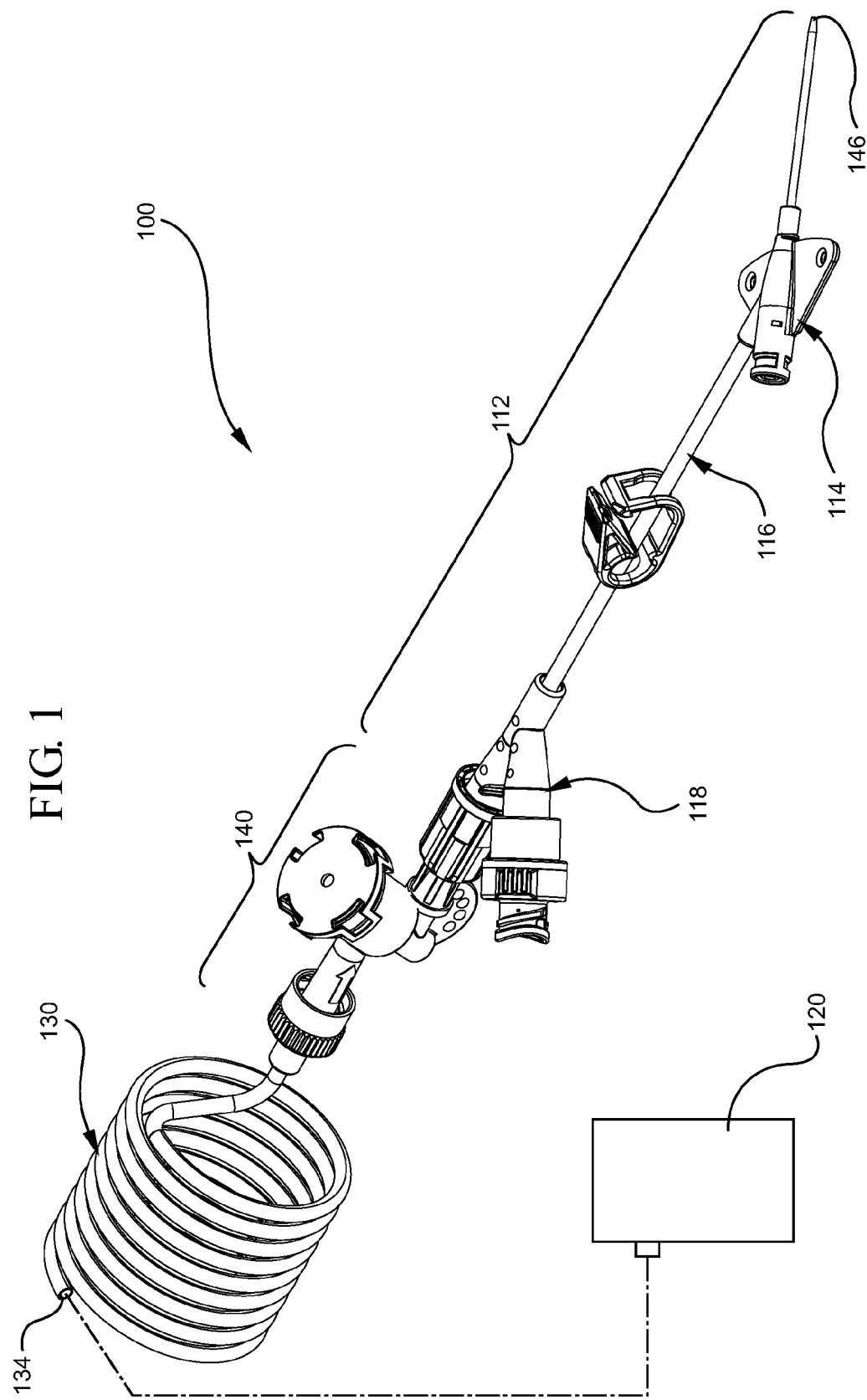
FIG. 1 is a perspective view of an infusion system in accordance with a representative embodiment of the present invention.

The systems and methods of the present invention are generally designed for use in combination with a vascular infusion system capable of rapidly delivering an infusate to the vascular system of a patient. Referring now to FIG. 1, a vascular infusion system 100 is shown, in accordance with a representative embodiment of the present invention. Infusion systems of this type are commonly configured to operate at internal pressures up to 2000 psi. Many systems operate in the range of 75 to 2000 psi, while specific devices of this type operate at 100, 200, and 300 psi. The vascular infusion system 100 comprises a vascular access device 112 coupled to an injector pump 120 via a coiled extension set 130. In some embodiments, the infusion system 100 further comprises a safety device 140 positioned between the vascular access device 112 and the injector pump 120. In some embodiments, a safety device 140 is provided to automatically occlude the fluid path of the infusion system 100, thereby preventing excessive pressure buildup in downstream infusion components.

An injector pump 120 generally comprises a fluid pumping apparatus configured to rapidly deliver an infusate, such as blood, medicaments, and CT scan contrast agents to a patient's vascular system. Desirable infusates may also include various fluids often of high viscosity as required for medical and diagnostic procedures. In some embodiments, the injector pump 120 comprises a power injector capable of delivering an infusate to a patient at flow rates from about 10 mL/hour up to greater than 1500 mL/minute. In some embodiments, a high infusion flow rate is desirable for medical procedures which require enhanced bolus density of an infusate in a patient's vascular system. For example, a trend in diagnostic imaging procedures is to utilize contrast media enhancement, which requires more viscous contrast media to be pushed into a patient at a higher flow rate, thereby resulting in increased image quality. Thus, in some embodiments an injector pump 120 and a vascular access device 112 are selected to compatibly achieve a desired infusion flow rate.

A coiled extension set 130 generally comprises flexible or semi-flexible polymer tubing configured to deliver an infusate from the injector pump 120 to the vascular access device 112. The extension set 130 includes a first coupler for connecting the extension set 130 to a downstream device 112 or 140. The extension set 130 also includes a second coupler 134 for connecting the extension set 130 to the injector pump 120. A coiled configuration of the extension set 130 generally prevents undesirable kinking or occlusion of the set 130 during infusion procedures. However, one of skill in the art will appreciate that the extension set 130 may include any configuration capable of efficiently delivering an infusate from an injector pump 120 to the patient via a vascular access device 112. In some embodiments, the extension set 130 is coupled between a syringe and a vascular access device whereby an infusate is manually injected into a patient. In other embodiments, the infusion system comprises only a syringe and a vascular access device, in accordance with the present invention.

The vascular access device 112 generally comprises a peripheral intravenous catheter 114. A peripheral intravenous catheter 114 in accordance with the present invention generally comprises a short or truncated catheter (usually 13 mm to 52 mm) that is inserted into a small peripheral vein. Such catheters generally comprise a diameter of approximately a 14 gauge catheter or smaller. Peripheral intravenous catheters 114 are typically designed for temporary placement. The short length of the catheter 114 facilitates convenient placement of the catheter but makes them prone to premature dislodging from the vein due to movement of the patient and/or recoil forces experienced during infusion procedures. Furthermore, unlike midline or central peripheral catheters, peripheral intravenous catheters 114 in accordance with the present invention comprise a tapered catheter tip 146 to accommodate use with an introducer needle (not shown) designed to aid in insertion of the catheter 114.

The tapered outer surface of the catheter tip 146 can provide a smooth transition between the narrow diameter of the catheter tip opening and the larger diameter of the catheter tubing. Thus, as the tip 146 of the catheter 114 is introduced into the vein of a patient, the tapered outer surface 146 facilitates easy insertion of the catheter 114 through the access hole. The tapered inner surface is generally provided to tightly contact the outer surface of an introducer needle housed within the lumen of the catheter. The introducer needle is provided to create an opening into the vein of patient through which the catheter tip is inserted. The tapered inner surface ensures a tight seal between the inner surface of the catheter and the outer surface of the needle. Following placement of the catheter, the introducer needle is removed.

An introducer needle is typically inserted through the catheter 114 such that a tip of the needle extends beyond the tapered tip 146. The tapered geometry of the tapered tip 146 conforms tightly to the outer surface of the introducer needle. Both the outer surface and the inner surface of the tip 146 are tapered towards the distal end of the catheter 114. The outer surface of the tip 146 is tapered to provide a smooth transition from the smaller profile of the introducer needle to the larger profile of the catheter outer diameter. Insertion of the introducer needle into the vein of the patient provides an opening into the vein through which the tapered tip 146 of the catheter 114 is inserted. The tapered outer surface of the tip 146 enables easy insertion of the catheter 114 into the opening. Once the peripheral intravenous catheter 114 is inserted into the vein of the patient, the introducer needle (not shown) is removed from the lumen of the catheter 114 to permit infusion via the catheter 114.

In some embodiments, an inner surface of the tip 146 is tapered to provide a secure seal between the inner surface of the catheter tip 146 and the outer surface of the introducer needle (not shown). Additionally, the tapered inner surface of the tip 146 causes an acceleration of infusate within the lumen of the catheter as the infusate nears and flows through the catheter tip 146. Following an infusion procedure, the peripheral intravenous catheter 114 is simply removed from vein and discarded.

A desired infusate is typically delivered to the catheter 114 via a section of intravenous tubing 116 coupled to the catheter 114. In some embodiments, a y-adapter 118 is coupled to an end of the tubing 116 opposite the catheter 114, enabling the vascular access device 112 to be coupled to the remainder of the vascular infusion system 100. One of skill in the art will appreciate the possible variations and specific features of available vascular access devices 112, as are commonly used in the medical and research professions. For example, in some embodiments a catheter 114 in accordance with the present invention may include additional access sites, clamps, parallel intravenous lines, valves, couplers, introducer needles, coatings, and/or materials as desired to fit a specific application.

Figure 2:
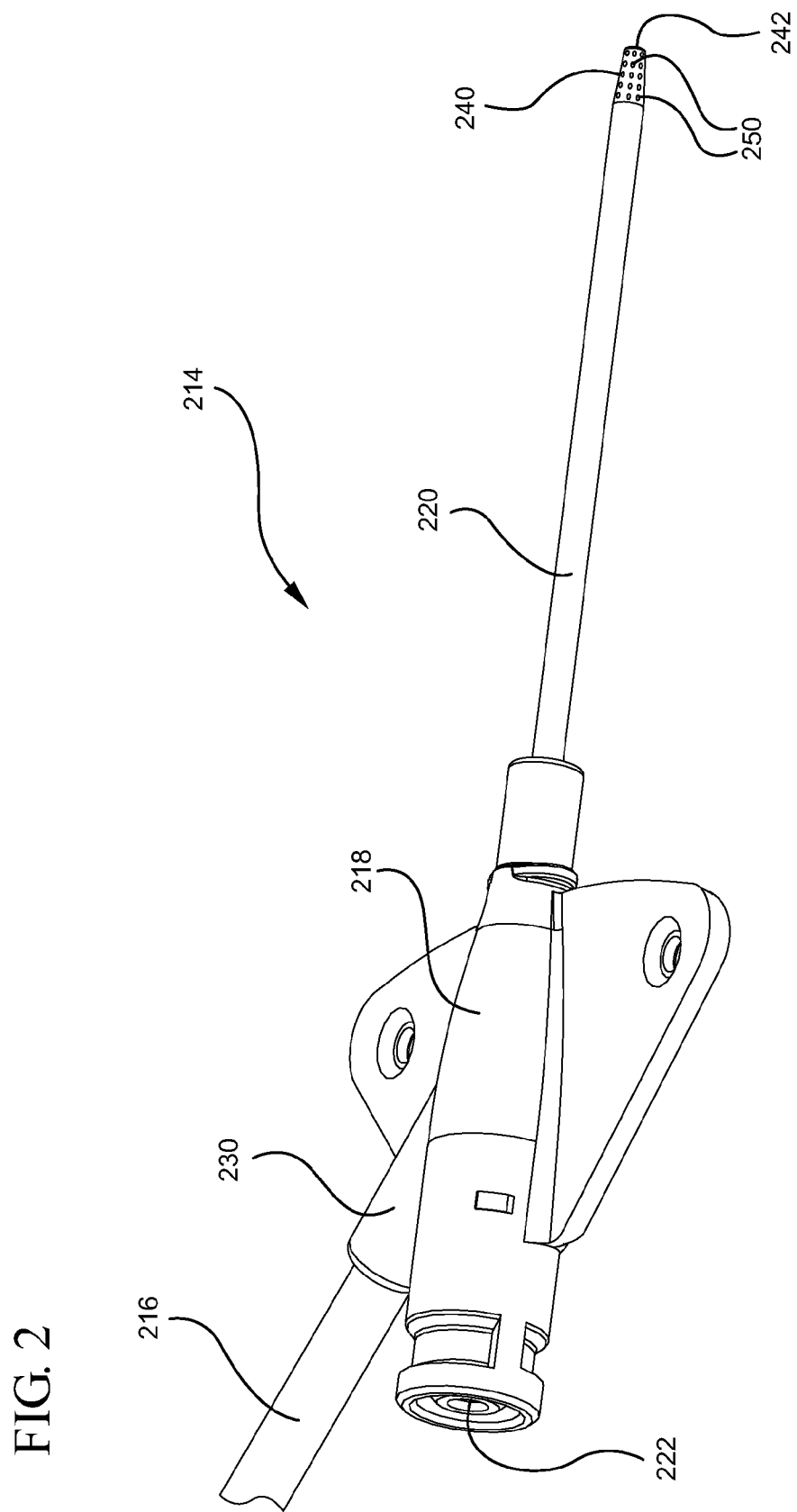
FIG. 2 is a detailed perspective view of a catheter with slits of its distal end in accordance with a representative embodiment of the present invention.

Referring now to FIG. 2, a catheter 214 is shown in accordance with a representative embodiment of the present invention. Catheter 214 generally comprises a catheter adapter 218 configured to house a tubular body member 220. Catheter adapter 218 further includes an inlet port 230 that is coupled to a section of intravenous tubing 216. The section of intravenous tubing 216 is further coupled to upstream infusion components, as shown and described in connection with FIG. 1, above.

The catheter adapter 218 facilitates delivery of an infusate within the intravenous tubing 216 to a patient via the tubular body member 220. An inner lumen of the catheter adapter 218 is in fluid communication with both an inner lumen of the intravenous tubing 216 and an inner lumen of the tubular body member 220. In some embodiments, catheter adapter 218 further comprises an access adapter 222. The access adapter 222 is generally provided to permit direct access to the inner lumen of the catheter adapter 218. In some embodiments, the access adapter 222 is accessed via a needle and a syringe to deliver an infusate to a patient via the tubular body member 220. In other embodiments, an introducer needle or guide wire is inserted into the access adapter 222 and advanced through the inner lumen of the tubular body member 220. In some embodiments, a tip portion of the introducer needle or guide wire (not shown) extends beyond a tip portion 240 of the tubular body member 220. As such, the tip portion of the introducer needle or guide wire may provide an opening into the vascular system of a patient into which the tubular body member 220 is inserted. Following placement of the tubular body member 220 into the vein of the patient, the introducer needle or guide wire is removed from the access adapter 222 thereby establishing fluid communication between the tubular body member 220, the catheter adapter 218 and the intravenous tubing 216.

In some embodiments, the tubular body member 220 is an intravenous catheter (or catheter body). The intravenous catheter 214 generally comprises a flexible or semi-flexible biocompatible material, as commonly used in the art. In some embodiments, the intravenous catheter 214 comprises a polymer material, such as polypropylene, polystyrene, polyvinylchloride, polytetrafluoroethylene, and the like. In other embodiments, the intravenous catheter 214 comprises a metallic material, such as surgical steel, titanium, cobalt steel, and the like.

The tubular body member 220 may comprise any length, where the length is selected based on the intended application of the catheter 214. For some applications, the tubular body member 220 is inserted into a peripheral vein of the patient. In other applications, the tubular body member 220 is inserted into a central vein of the patient.

For rapid infusion applications, the tip portion 240 of the tubular body member 220 is modified to include a splittable feature 250. Splittable feature 250 generally allows the catheter tip 240 to open up or split apart when an infusate is injected through catheter 214 at high pressure. As such, the tapered inner and outer surface geometries of catheter tip 240 are expanded thereby eliminating any geometric constriction that would otherwise increase the flow velocity exiting the distal opening 242 of the tubular body member's lumen. Accordingly, for some embodiments the force needed to open splittable feature 250 is less than the force exerted on catheter tip 240 by the infusate during high pressure infusion procedures.

Figure 3:
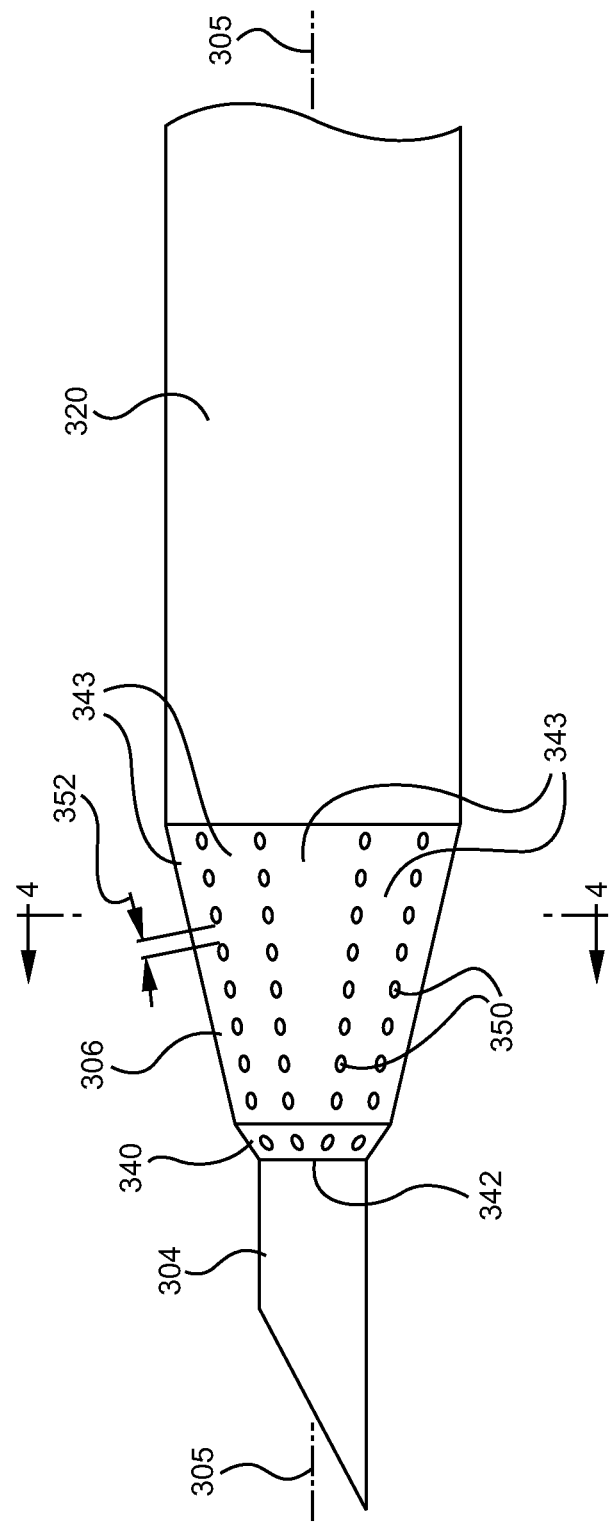
FIG. 3 is a perspective view of a catheter tip having slits and an introducer needle extending therethrough in accordance with a representative embodiment of the present invention.

In some embodiments, splittable feature 250 comprises a closed position prior to being inserted into the vasculature of a patient, as shown in FIG. 2. The closed position of splittable feature 250 enables effective insertion of venous catheter 214, as discussed above. In particular, the closed position ensures that a close tolerance is maintained between distal opening 342 and an outer surface of the introducer needle 304, as shown in FIG. 3. Thus, catheter tip 340 is able to be easily inserted into the patient's vasculature via an opening provided by the introducer needle. Further, the absence of large diffusion holes provides a continuous outer surface for tubular body 320, thereby preventing any snagging or catching of tubular body 320 on the skin or other tissues of the patient during catheterization. Still further, the absence of large diffusion holes maintains the structural rigidity of catheter tip 340, thereby preventing any undesirable crushing or collapsing of catheter tip 340 during the catheterization procedure.

Figure 4:
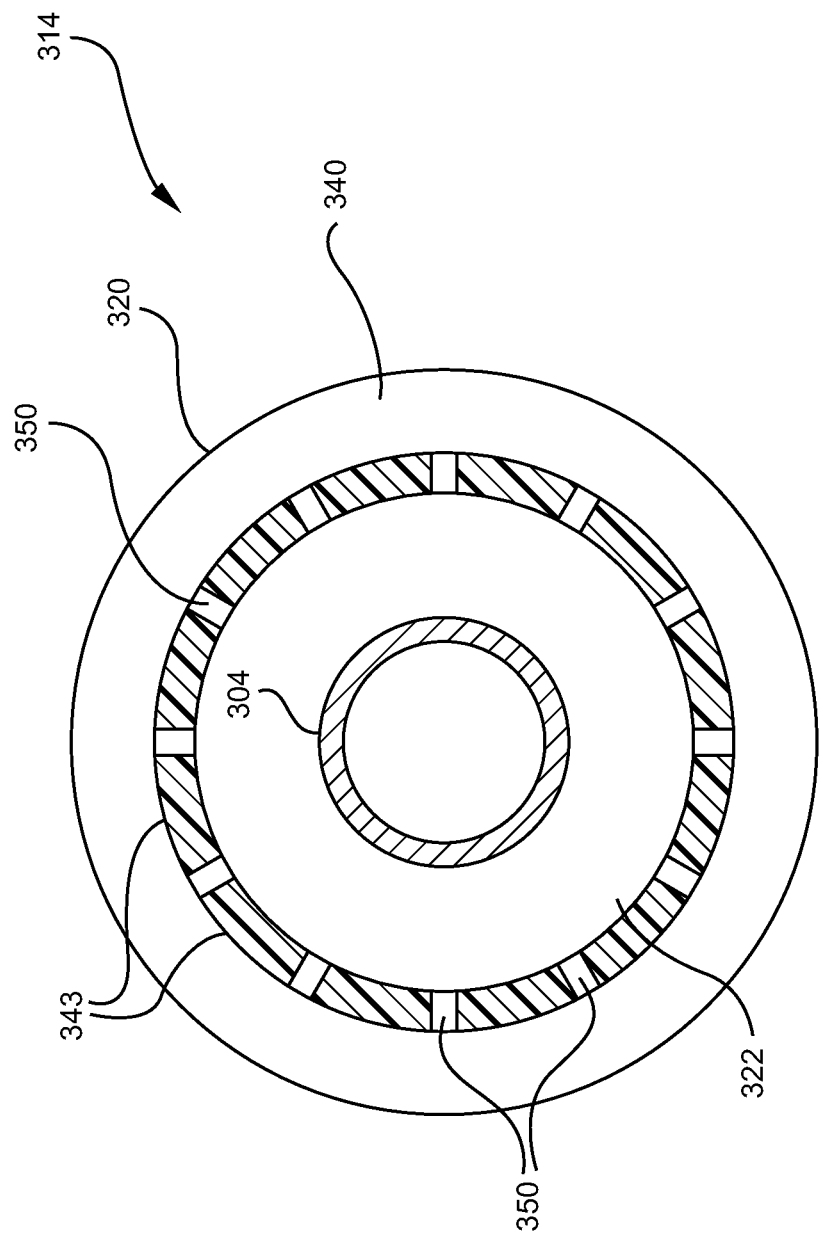
FIG. 4 is a cross section end view of a cannula and catheter prior to fluid infusion in accordance with a representative embodiment of the present invention
Figure 5:
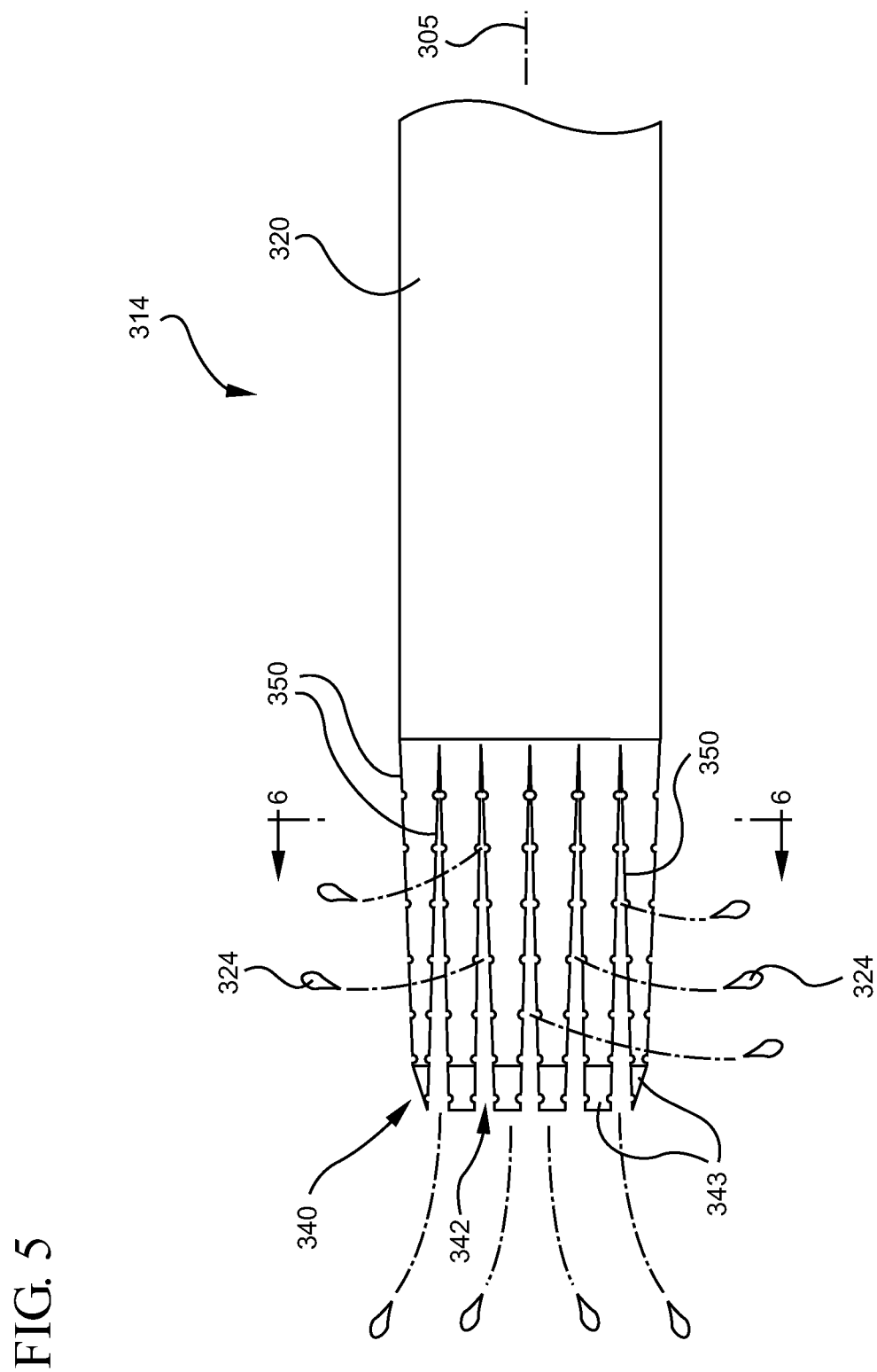
FIG. 5 is a perspective side view of a catheter tip following fluid infusion in accordance with a representative embodiment of the present invention.
Figure 6:
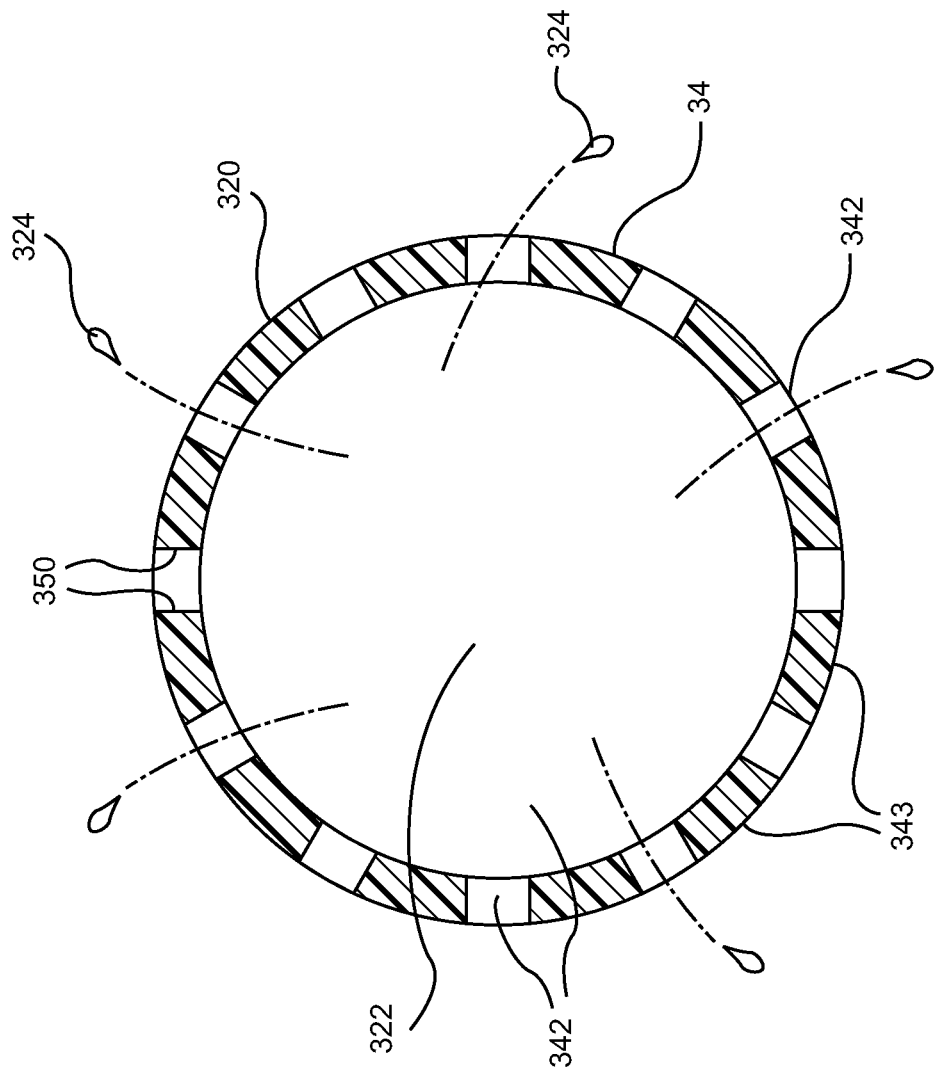
FIG. 6 is a cross section end view of the catheter tip of FIG. 5 in accordance with a representative embodiment of the present invention.

With continued reference to FIGS. 3 and 4, in some embodiments splittable feature 350 divides catheter tip 340 into a plurality of adjacent fingers or sections 343. When in the closed position, as shown, the plurality of adjacent fingers 343 are connected via splittable feature 350 thereby forming the closed catheter tip 340. In some embodiments, splittable feature 350 comprises a line of perforation openings or holes interposed between adjacent fingers 343. A space 352 between adjacent proximal and distal openings is selected so as to facilitate tearing or separation of the catheter tip material between adjacent proximal and distal openings. Accordingly, when subjected to increased pressures within catheter body lumen 322, splittable features 350 separate thereby assuming an open position which forms a plurality of separated, adjacent fingers 343, as shown in FIGS. 5 and 6.

In some embodiments, splittable features 350 are axially oriented, and therefore approximately parallel to a longitudinal axis 305 of catheter 314. In the open position, the plurality of separated fingers 343 enlarge the effective area of distal catheter opening 342 by providing a plurality of extended slits or tapered openings through which an infusate 324 exits lumen 322. Once the splittable features 350 have been separated, any geometric or structural constriction of tip 340 are eliminated. As such, inner lumen pressures caused by infusate 324 are reduced and/or eliminated, thereby producing laminar, low pressure flow of infusate 324 through tubular body 320 and catheter tip 340.

Figure 7:
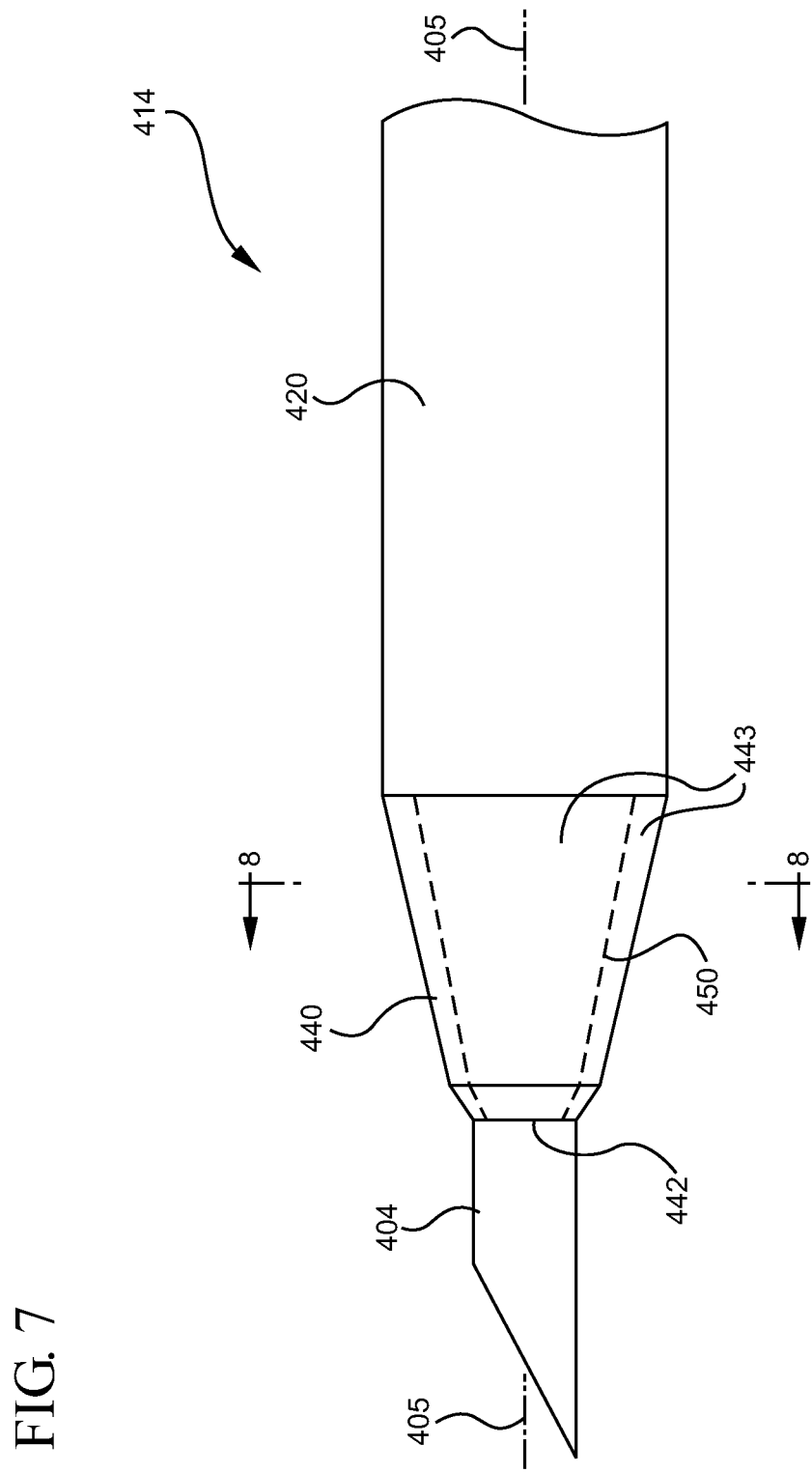
FIG. 7 is a perspective side view of a cannula and catheter prior to fluid infusion in accordance with a representative embodiment of the present invention.
Figure 8:
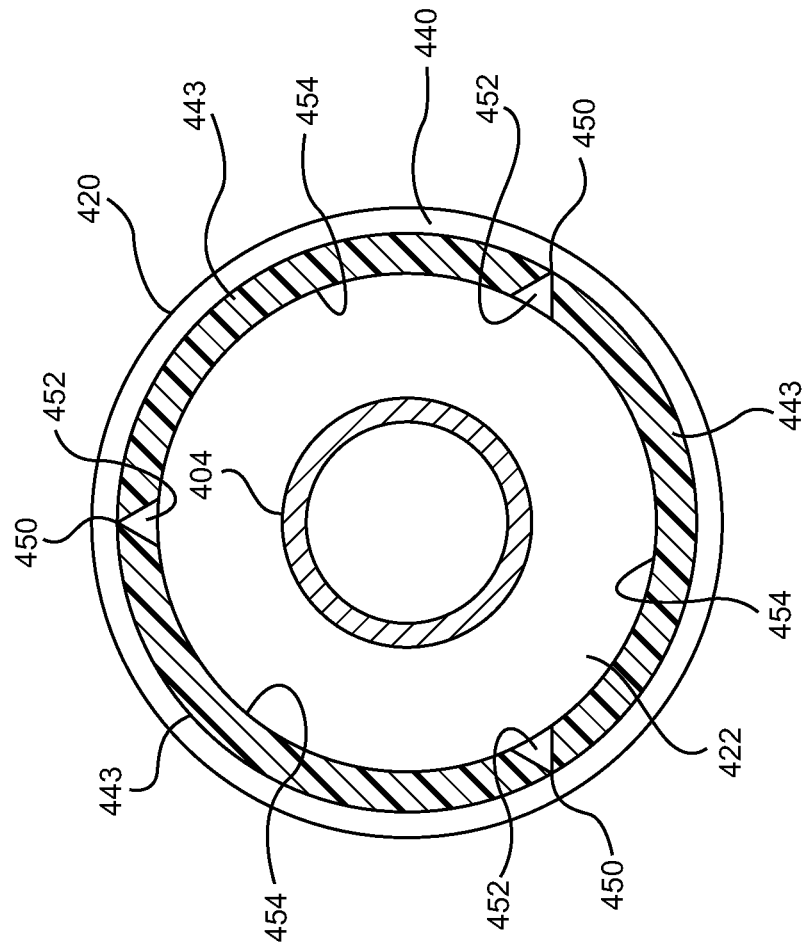
FIG. 8 is a cross section view of the catheter tip of FIG. 7 in accordance with a representative embodiment of the present invention.
Figure 9:
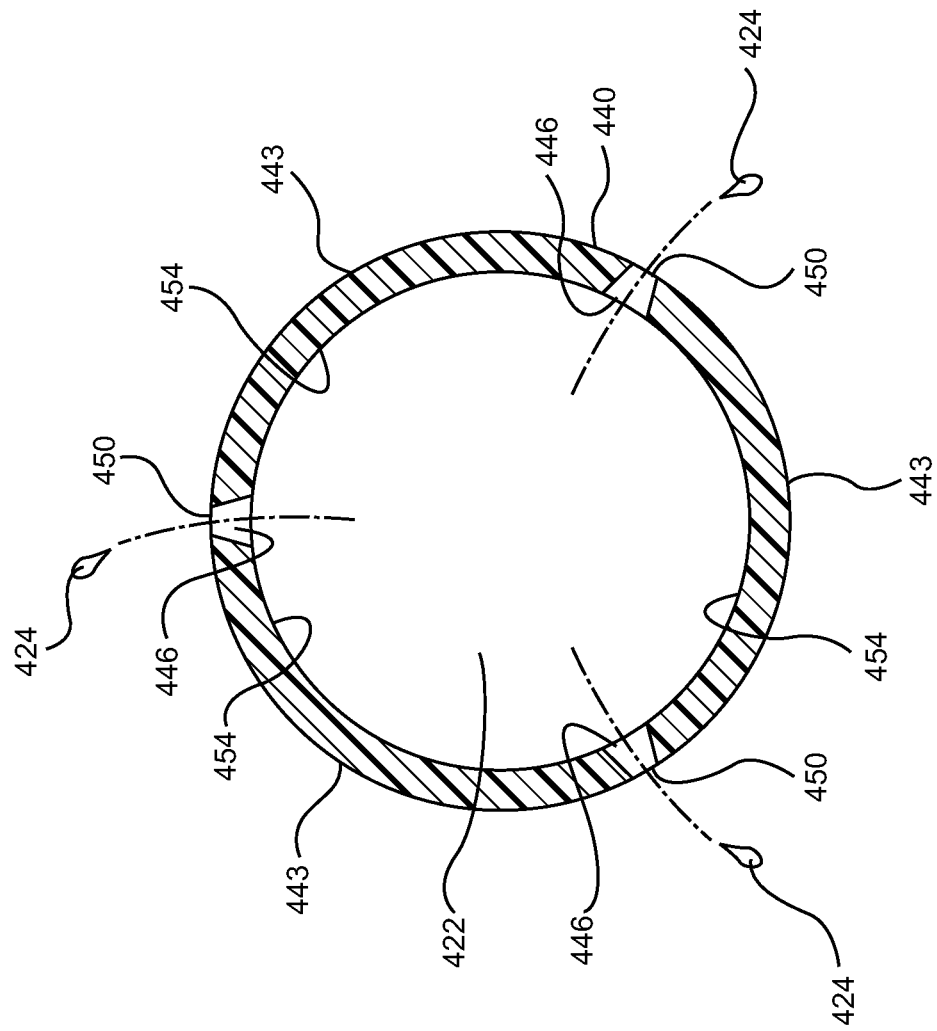
FIG. 9 is a cross section end view of the catheter tip of FIG. 8 following removal of the cannula and following fluid infusion in accordance with a representative embodiment of the present invention.

In some embodiments, splittable feature 450 comprises a plurality of skive lines formed on an inner surface of the tip portion 440 of tubular body 420 of catheter 414, as shown in FIGS. 7-9. In some embodiments, splittable feature 450 is provided so as to divide catheter tip 440 into a plurality of adjacent fingers or sections 443. By locating splittable feature 450 on the inner surface of catheter tip 440, tip 440 maintains a continuous outer surface thereby preventing any snagging or catching of catheter tip 440 on the skin or tissues of the patient during insertion of the catheter into the vasculature of the patient. However, in some embodiments splittable feature 450 comprises a plurality of skive lines formed on an outer surface of tip portion 440. Further, in some embodiments splittable feature 450 comprises one or more skive line or lines formed on either the outer surface, the inner surface, or both the outer and inner surfaces of tip portion 440.

When in the closed position, as shown in FIGS. 7 and 8, the plurality of adjacent fingers 443 are connected via splittable feature 450 thereby forming the closed catheter tip 440. As such, splittable feature 450 forms a plurality of grooves 452 axially oriented, and therefore approximately parallel to a longitudinal axis 405 of catheter 414. In some embodiments, the axial orientation of grooves 452 provides a plurality of axially oriented ribs or splines 454 which facilitate a more laminar fluid flow of the infusate through catheter lumen 422. Further, in some embodiments grooves 452 provide an increased effective inside diameter of catheter tip 440. Each of these features, alone or in combination reduces turbulent flow of the infusate, thereby encouraging laminar flow and increasing the effective rate of flow for the infusate.

An apex of each groove 452 comprises a thin webbing of catheter material having a thickness selected such that the thin webbing is defeated in response to increased pressure within catheter body lumen 422 during high pressure and/or high velocity infusion procedures. When defeated, splittable feature 450 divides catheter tip 440 into a plurality of separated, adjacent fingers 443 thereby enlarging the effective surface area of distal catheter opening 442 by providing a plurality of extended slits or tapered openings 446 through which an infusate 424 exits lumen 422, as shown in FIG. 9.

Splittable features of the present invention may include any structure, geometry, mechanical function or other mechanism whereby to eliminate a constrictive structure of a catheter tip by expanding the effective area of the distal end opening when exposed to an increased inner lumen pressure. For example, splittable features in accordance with the present invention may include non-linear configurations, as taught in U.S. patent application Ser. No. 13/053,495, incorporated herein by reference.

Splittable features in accordance with the present invention may include engineered points of weakness within the catheter body and/or catheter tip that are designed to be defeated in response to increased inner lumen pressure during infusion procedures. In some embodiments, a catheter comprises a single splittable feature. In other embodiments, a catheter comprises two or more splittable features. Accordingly, when subjected to increased inner lumen pressure, some catheters of the present invention provide a single finger wherein a single splittable feature is defeated thereby forming a single extended slit or tapered opening through which an infusate exits the lumen of the catheter. In other embodiments, when subjected to increased inner lumen pressure, some catheters of the present invention provide two or more adjacent fingers, wherein two or more splittable features are defeated thereby forming two or more extended slits or tapered openings through which an infusate exits the lumen of the catheter.

In general, splittable features of the present invention are designed to comprise sufficient structural integrity to maintain the closed position of the catheter tip during insertion of the catheter into the vasculature of the patient. In particular, splittable features of the present invention are provided which are capable of withstanding compressive forces exerted on the catheter tip during insertion into the patient. However, splittable features of the present invention are further designed to be defeated when exposed to increased inner lumen pressures within the tip portion of the catheter under a high pressure application.

Catheters comprising splittable features in accordance with the present invention may be provided by any known methods in the art. In some embodiments, splittable features of the present invention are provided by molding the splittable feature into the catheter tubing during the tip forming process. For example, splittable features of the present invention may be provided by an injection molding process, use of mechanical processes, and/or via use of a laser. In particular, a desired geometry for making the splittable feature can be included in a tipping mandrel, a tipping die, or both, as well as within the core pin, mold cavity, or both, used to produce and/or manufacture the catheter device.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A vascular access device, comprising:
   a catheter adapter having an access adapter, an inlet port, and a section of intravenous tubing having a first end that is coupled to the inlet port and a second end that is coupled to an adapter, the adapter being configured to connect the catheter adapter to an injector pump;
   a catheter extending from a distal end of the catheter adapter, the catheter comprising:
      a catheter body having an outer surface, an inner surface, a proximal end, a distal end, a lumen extending between the proximal and distal ends along a longitudinal axis of the catheter body, and a distal lumen opening, the lumen of the catheter body being in fluid communication with the access adapter and the inlet port of the catheter adapter;
      a catheter tip forming a portion of the distal end, the catheter tip including the distal lumen opening; and
      a splittable feature formed within a wall of the catheter tip, the splittable feature comprising a plurality of skive lines formed along an inner surface of the wall, each of the plurality of skive lines extending sufficiently into the inner surface of the wall so that, when fluid is injected by the injector pump through the lumen while the catheter tip is inserted into the vasculature of a patient, pressure applied on the inner surface by the fluid causes the skive lines to split thereby transforming the catheter tip into a plurality of separated fingers; and
   an introducer needle extending through the access adapter of the catheter adapter and through the lumen of the catheter such that a tip of the introducer needle extends out through the distal lumen opening of the catheter tip, an inner diameter of the catheter tip conforming tightly to an outer surface of the introducer needle.

2. The catheter of claim 1, wherein the splittable feature comprises three or more skive lines such that the catheter tip is transformed into three or more separated fingers by the pressure applied on the inner surface of the wall by the fluid.

3. The catheter of claim 1, wherein the splittable feature further comprises one or more skive lines formed along an outer surface of the wall.

4. The catheter of claim 1, further comprising:
   one or more axial ribs or splines formed along the inner surface of the wall.

5. A vascular access device comprising:
   a catheter adapter having an access adapter, an inlet port, and a section of intravenous tubing having a first end that is coupled to the inlet port and a second end that is coupled to an adapter, the adapter being configured to connect the catheter adapter to an injector pump;
   a catheter extending from a distal end of the catheter adapter, the catheter comprising:
      a catheter body having an outer surface, an inner surface, a proximal end, a distal end, a lumen extending between the proximal and distal ends along a longitudinal axis of the catheter body, and a distal lumen opening, the lumen of the catheter body being in fluid communication with the access adapter and the inlet port of the catheter adapter;
      a catheter tip forming a portion of the distal end, the catheter tip including the distal lumen opening; and
      a splittable feature formed within a wall of the catheter tip, the splittable feature comprising a plurality of lines of perforation openings, each perforation opening in a line being separated from another proximally or distally positioned perforation opening in the line by a space of catheter tip material, the space being configured to tear due to an increased pressure applied against an inner surface of the wall by fluid when the fluid is injected by the injector pump through the catheter tip while the catheter tip is inserted into the vasculature of a patient thereby transforming the catheter tip into a plurality of separated fingers; and
   an introducer needle extending through the access adapter of the catheter adapter and through the lumen of the catheter such that a tip of the introducer needle extends out through the distal lumen opening of the catheter tip, an inner diameter of the catheter tip conforming tightly to an outer surface of the introducer needle.

6. The catheter of claim 5, wherein the splittable feature comprises three or more lines of perforation openings such that the catheter tip is transformed into three or more separated fingers by the pressure applied on the inner surface of the wall by the fluid.

7. The catheter of claim 5, wherein the splittable feature comprises six or more lines of perforation openings such that the catheter tip is transformed into six or more separated fingers by the pressure applied on the inner surface of the wall by the fluid.

8. The catheter of claim 5, further comprising:
   one or more axial ribs or splines formed along the inner surface of the wall.

9. The catheter of claim 5, wherein at least some of the perforation openings extend completely through the wall of the catheter tip.

10. The catheter of claim 5, wherein each of the perforation openings extends completely through the wall of the catheter tip.

11. A vascular access device, comprising:
   a catheter adapter having an access adapter, an inlet port, and a section of intravenous tubing having a first end that is coupled to the inlet port and a second end that is coupled to an adapter, the adapter being configured to connect the catheter adapter to an injector pump;
   a catheter extending from a distal end of the catheter adapter, the catheter comprising:
      a catheter body having a proximal end, a distal end, a lumen extending from the distal end to the proximal end, and a distal lumen opening, the catheter body further having a truncated length sufficient to access a peripheral vein of a patient, the catheter body being sized smaller than or equal to a fourteen gauge catheter, the lumen of the catheter body being in fluid communication with the access adapter and the inlet port of the catheter adapter;
      a splittable feature formed through a distal, tapered portion of the catheter body, the splittable feature comprising a plurality of skive lines extending sufficiently into an inner surface of the distal, tapered portion so that, when fluid is injected by the injector pump through the distal, tapered portion while the distal, tapered portion is inserted into the vasculature of a patient, pressure applied on the inner surface by the fluid causes the skive lines to split thereby transforming the distal, tapered portion into a plurality of separated fingers; and an introducer needle extending through the access adapter of the catheter adapter and through the lumen of the catheter such that a tip of the introducer needle extends out through the distal lumen opening of the catheter, an inner diameter of the catheter conforming tightly to an outer surface of the introducer needle.

12. The peripheral catheter of claim 11, wherein the splittable feature comprises three or more skive lines such that the distal, tapered portion is transformed into three or more separated fingers by the pressure applied on the inner surface by the fluid.

13. The peripheral catheter of claim 11, wherein the splittable feature further comprises one or more skive lines formed along an outer surface of the distal, tapered portion.

14. The peripheral catheter of claim 11, further comprising:

one or more axial ribs or splines formed along the inner surface of the distal, tapered portion.

* * * * *